US006265571B1

(12) United States Patent
Shi et al.

(10) Patent No.: US 6,265,571 B1
(45) Date of Patent: Jul. 24, 2001

(54) PURIFICATION PROCESS FOR ANTI-PARASITIC FERMENTATION PRODUCT

(75) Inventors: Qian Shi, Chapel Hill; John A. Hill, Durham, both of NC (US)

(73) Assignees: Magellan Laboratories, Inc., Research Triangle Park; Blue Ridge Pharmaceuticals, Greensboro, both of NC (US)

( * ) Notice: Subject to any disclaimer, the term of this patent is extended or adjusted under 35 U.S.C. 154(b) by 0 days.

(21) Appl. No.: 09/351,751

(22) Filed: Jul. 12, 1999

(51) Int. Cl.$^7$ ...................................................... C07H 1/00
(52) U.S. Cl. ............................................. 536/127; 536/7.1
(58) Field of Search ...................................... 536/7.1, 127

(56) References Cited

U.S. PATENT DOCUMENTS

| 4,333,925 | 6/1982 | Buhs et al. . |
| 4,429,042 | 1/1984 | Albers-Schonberg et al. . |
| 4,668,696 | 5/1987 | Goegelman et al. . |
| 4,927,918 | 5/1990 | Banks et al. . |
| 4,929,638 | 5/1990 | Dutton et al. . |
| 5,077,398 | 12/1991 | Matthews . |
| 5,212,322 | 5/1993 | Okazaki et al. . |
| 5,234,831 | 8/1993 | Hafner et al. . |
| 5,556,868 | 9/1996 | Banks . |
| 5,565,359 | 10/1996 | Hafner et al. . |
| 5,576,199 | 11/1996 | Hafner et al. . |
| 5,656,748 | * 8/1997 | Arit et al. ............................ 536/124 |
| 5,677,322 | 10/1997 | Banks . |
| 5,723,488 | 3/1998 | Walshe . |
| 5,733,887 | 3/1998 | Walshe . |

FOREIGN PATENT DOCUMENTS

| 0 059 616 | 9/1982 | (EP) . |
| 0 059 616 | 7/1985 | (EP) . |
| 0 253 767 | 6/1987 | (EP) . |
| 0 524 686 | 1/1993 | (EP) . |
| WO 98/38201 | 9/1998 | (WO) . |

OTHER PUBLICATIONS

Cobin et al., "Determination of Total Avermectin B–1 and 8,9–Z–Avermectin B–1 Residues in Wine by Liquid–Chromatography," Journal of AOAC International, vol. 79 (No. 5), pp. 1158–1161, (1996) (Abstract only).

Li et al., "Determination of Avermectin B–1 in Biological Samples by Immunoaffinity Column Cleanup and Liquid–Chromatography with UV Detection," Journal of AOAC International, vol. 79 (No. 5), pp. 1062–1067, (1996) (Abstract only).

Cobin et al., "Liquid–Chromatographic Method for Determination of Total Avermectin B–1 and 8,9–Z–Avermectin B–1 Residues in Hops," Journal of AOAC International, vol. 79 (No. 2), pp. 503–507, (1996) (Abstract only).

Cobin et al., "Liquid–Chromatographic Method for Rapid-Determination of Total Avermectin B–1 and 8,9–Z–Avermectin B–1 Residues in Apples," Journal of AOAC International, vol. 78 (No. 2), pp. 419–423, (1995) (Abstract only).

Bernal et al., "HPLC Determination of Residual Ivermectin in Cattle Dung Following Subcutaneous Injection," Journal of Liquid Chromatography, vol. 17 (No. 11), pp. 2429–2444, (1994) (Abstract only).

Antonian et al., "An Automated Method for the Determination of Subnanogram Concentrations of Eprinomectin in Bovine Plasma," Journal of Pharmaceutical and Biomedical Analysis, vol. 16 (No. 8), pp. 1363–1371, (1998) (Abstract only).

Li et al., "Immunoaffinity Column Cleanup Procedure for Analysis of Ivermectin in Swine Liver," Journal of Chromatography, vol. 696, (No. 1), pp. 166–171, (1997) (Abstract only).

Chapman, "Some Limitations to Modeling Pesticide Disappearance from Soil Based on Nonlinear–Regression of Concentration–Time Data," Journal of Environmental Science and Health Part B–Pesticides Food Contaminants and Agricultural Wastes, vol. 27 (No. 6), pp. 655–676, (1992) (Abstract only).

Chiou et al., "Determination of Ivermectin in Human Plasma and Milk by High–Performance Liquid Chromatography with Fluorescence Detection," J. Chromatogr., Biomed. Appl., vol. 60 (No. 1), (1987) (Abstract only).

* cited by examiner

Primary Examiner—Elli Peselev
(74) Attorney, Agent, or Firm—Jenkins & Wilson, P.A.

(57) ABSTRACT

A process for purifying the bacterial fermentation product ivermectin, particularly for use as a reference standard compound in a governmental regulatory approval process. The process includes the use of reversed-phase flash column chromatography coupled with gradient elution. An exemplary eluent mixture includes acetonitrile, methanol and water.

15 Claims, No Drawings

PURIFICATION PROCESS FOR ANTI-PARASITIC FERMENTATION PRODUCT

TECHNICAL FIELD

The present invention relates generally to an improved process for the purification of a product derived from bacterial fermentation. More particularly, the present invention relates to a method for purifying ivermectin, a bacterial fermentation product having anti-parasitic activity.

| Table of Abbreviations | |
|---|---|
| Am | amount |
| DI | deionized |
| DSC | differential scanning calorimetry |
| FAB | fast atom bombardment |
| FID | flame ionization detector |
| GC | gas chromatography |
| HPLC | high performance liquid chromatography |
| IR | infrared |
| MS | mass spectrometry |
| NMR | nuclear magnetic resonance |
| PF | Pharmacopeial Forum |
| TGA | thermal gravimetric analysis |
| TLC | thin layer chromatography |
| USP | U.S. Pharmacopeia |
| UV | ultraviolet |
| XRPD | x-ray powder diffraction |
| % AUC | percent area under the curve |

BACKGROUND ART

It will be appreciated by those of skill in the art that the process of obtaining governmental regulatory approval of a composition of matter for use as a therapeutic agent in both animal and human patients is an arduous and complex process. One particular aspect of the process pertains to proving and establishing the molecular structure of the chemical entity for which regulatory approval is sought. To establish the molecular structure of a candidate chemical entity to the satisfaction of regulatory approval bodies, it is critically important to have a highly purified reference standard compound against which lots or batches of the candidate compound are compared during the process of proving and establishing the structure.

Additionally, a highly purified reference standard for a compound is very important to quantification aspects of the compound. As is known to one of skill in the art, aspects of quantification include in vitro release and stability data. If a highly pure reference standard for a candidate compound is used, high quality data concerning stability and potency can be produced for submission to a regulatory body. The submission of such data ultimately leads to the development and distribution of better and safer products to the consumer. Thus, the provision of a highly purified reference standard is a key point in the regulatory approval process for candidate therapeutic compounds. Indeed, the highly purified reference standard is the standard to which all development activity materials are critically compared.

It will further be appreciated by one of skill in the art that it is difficult to provide highly pure reference standards for compounds initially isolated as bacterial fermentation products. First of all, the presence of contaminants in the bacterial fermentation product makes the basic structure of the chemical entity of interest difficult to ascertain. Moreover, once a chemical structure is determined, the presence of myriad polar and/or non-polar contaminants make it very difficult to purify the compound to a form suitable for use as a therapeutic agent. More particularly, it is very difficult to purify a reference standard quality compound for use in regulatory approval processes.

A compound of particular interest is ivermectin, a bacterial fermentation product having anti-parasitic activity and which is used in the treatment of heart worms. Ivermectin is typically prepared as a fermentation product from *Streptomyces avermitilis* coupled with a "semi-synthesis" chemical reaction. By "semi-synthesis" is meant synthetic transformations carried out on a previously naturally-formed structure. Ivermectin is included within the general class of fermentation product compounds known as avermectins. Despite the recognized utility of ivermectin in the treatment of heart worms, particularly in horses, regulatory approval processes are made difficult by the lack of a highly purified reference standard ivermectin compound.

The disclosures of all the following patents are incorporated herein by reference.

U.S. Pat. No. 4,429,042 issued to Albers-Schonberc et al. on Jan. 31, 1984 (assignee Merck & Co., Inc.) discloses the isolation of ivermectin from fermentation media. Purification is described as optionally accomplished by chromatographic techniques including normal phase column chromatography utilizing silica gel, aluminum oxide, dextran gels, and the like, coupled with elution with various solvents. High performance liquid chromatography (HPLC) is also described as an optional chromatographic detection method.

U.S. Pat. No. 4,333,925 issued to Buhs et al. on Jun. 8, 1982 (assignee Merck & Co., Inc.) discloses derivatives of ivermectin compounds which are purified from the livers of animals that have been administered ivermectin, as well as from in vitro incubations of such compounds with animal liver preparations. Isolation and purification of the derivatives are carried out using solvent extraction and chromatographic techniques, including HPLC.

U.S. Pat. No. 5,077,398 issued to Matthews on Dec. 31, 1991 (assignee Merck & Co., Inc.) discloses a process for the isolation and purification of avermectin compounds, particularly avermectin B1 and B2, which have significant anti-parasitic activity. Crystallization and re-crystallization techniques which facilitate the crystallization, isolation and purification of avermectin B1 and B2 are discussed. Difficulties associated with separating B1a/B1b and B2a/B2b homologs are noted.

What is needed is an improved method for purifying the bacterial fermentation product ivermectin which produces a highly purified product, yet is simple in operation and practice. Despite the above-described efforts, such a method is not currently available in the art.

DISCLOSURE OF THE INVENTION

A process for purifying ivermectin is disclosed. Substantially purified ivermectin produced by the process is also disclosed. The process comprises obtaining substantially impure ivermectin; loading the substantially impure ivermectin on a chromatographic column suitable for reversed-phase flash column chromatography; initiating reversed-phase flash chromatography by applying a first volume of an eluent mixture to the column, the eluent mixture comprising acetonitrile, a lower alkyl alcohol and water; establishing an eluent gradient in the column by adding a series of subsequent volumes of the acetonitrile/lower alkyl alcohol/water eluent mixture to the column, wherein each of the first and the subsequent volumes of the eluent mixture has a ratio of acetonitrile to lower alkyl alcohol to water that varies according to a predetermined profile; and collecting predetermined fractions eluted from the column, the predetermined fractions including substantially purified ivermectin.

Accordingly, it is an object of the present invention to provide an improved process for purifying ivermectin that is highly effective but yet does not require complex equipment or elaborate process steps.

It is another object of the present invention to provide an improved process for purifying ivermectin which yields a purified product suitable for use as a reference standard in a regulatory approval process.

It is another object of the present invention to provide a purification process for ivermectin which enriches the resulting purified ivermectin mixture with respect to a particular ivermectin homolog.

It is a further object of the present invention to provide an improved purification process for ivermectin which utilizes gradient elution and reversed-phase flash column chromatography.

Some of the objects of the invention having been stated hereinabove, other objects will become evident as the description proceeds, when taken in connection with the accompanying Laboratory Examples as best described hereinbelow.

DETAILED DESCRIPTION OF THE INVENTION

A process for purifying ivermectin is disclosed in accordance with the present invention. The process comprises obtaining substantially impure ivermectin; loading the substantially impure ivermectin on a chromatographic column suitable for reversed-phase flash column chromatography; initiating reversed-phase flash chromatography by applying a first volume of an eluent mixture to the column, the eluent mixture comprising acetonitrile, a lower alkyl alcohol and water; establishing an eluent gradient in the column by adding a series of subsequent volumes of the acetonitrile/lower alkyl alcohol/water eluent mixture to the column, wherein each of the first and the subsequent volumes of the eluent mixture has a ratio of acetonitrile to lower alkyl alcohol to water that varies according to a predetermined profile; and collecting predetermined fractions eluted from the column, the predetermined fractions including substantially purified ivermectin.

The terms "normal-phase flash chromatography" and "reversed-phase flash column chromatography" are believed to have well-established meanings in the art. To facilitate explanation of the present invention, as used herein the term "normal-phase flash chromatography" is meant to refer to standard column chromatography wherein the stationary phase is polar, and initially a less polar eluent is utilized as the mobile phase and is then followed by more polar eluents. In contrast, the term "reversed-phase flash chromatography" is meant to refer to column chromatography wherein the stationary phase is non-polar, and for the mobile phase, the initial eluent is a more polar eluent and subsequent eluents are less polar. Both normal-phase and reversed-phase flash chromatography are typically performed at room temperature and pressure slightly greater than atmospheric pressure.

As used herein and in the claims, the term "lower alkyl alcohol" is meant to refer to an alcohol preferably selected from lower alkyl alcohols having 1 to 4 carbon atoms, for example, methyl, ethyl, n-propyl, isopropyl, n-butyl and isobutyl alcohols. As described hereinbelow, methanol is a preferred example of a lower alkyl alcohol for use in the eluent mixture in accordance with the present invention.

The method of the present invention includes the use of a chromatographic column suitable for reversed-phase flash column chromatography. An exemplary medium for the chromatographic column comprises octadecyl ($C_{18}$) silica gel. Additional media for the column would be apparent to one of skill in the art (e.g., octyl ($C_8$) silica gel, phenyl silica gel), given that the choice of the medium typically depends on the substance to be purified.

By the term "predetermined profile", as used with respect to the ratio of eluents within the eluent mixture used in the method of the present invention, it is meant to refer to a profile of ratios among components of the eluent mixture. Particularly, the ratios change as subsequent volumes of eluent mixture are added to a column such that an amount of a particular component as compared to an amount of another component may be reduced and/or increased in the subsequent volume of eluent mixture. Further, as would be apparent to one of ordinary skill in the art, the ratios of components of the eluent mixtures can vary, for example, in accordance with the selected lower alkyl alcohol and in accordance with a desired elution gradient as exemplified hereinbelow.

For example, in a preferred embodiment of the present invention, the ratio of acetonitrile to lower alkyl alcohol to water initially comprises 0:5:5 in a first volume of eluent mixture. A subsequent volume of eluent mixture then comprises acetonitrile and lower alkyl alcohol and water in the following ratio, 5:2:3. A subsequent volume of the acetonitrile/lower alkyl alcohol/water eluent mixture comprises 5:2.5:2.5. Another subsequent volume of the acetonitrile/lower alkyl alcohol/water eluent mixture comprises a ratio of 5:3:2. A final volume of acetonitrile/lower alkyl alcohol/water eluent mixture comprises a ratio of 5:3:1. In a more preferred embodiment of the present invention, a similar profile is followed, and the lower alkyl alcohol comprises methanol.

An even more preferred predetermined profile of ratios of acetonitrile to methanol to water in the subsequent volumes of eluent mixture comprises ratios that range from 0:5:5 to 5:4:1. The predetermined fractions collected from the column preferably correspond to volumes of eluent mixture wherein the acetonitrile, methanol and water are present in the eluent mixture in the following ratios, 5:2:3, 5:3:2, 5:3:1 and 5:4:1. More preferably, the predetermined fractions collected from the column correspond to volumes of eluent mixture wherein the acetonitrile, methanol and water are present in the eluent mixture in the following ratios, 5:3:2 and 5:3:1.

As used herein and in the claims, by the terms "substantially purified" or "substantially pure", applicants mean to encompass an ivermectin product having a purity level of at least about 96%, more preferably of at least about 97%, more preferably still of at least about 98%, and even more preferably still of at least about 99%. Methods for establishing purity levels are disclosed hereinbelow and are known in the art. Correspondingly, the terms "substantially unpurified" or "substantially impure" are meant to refer to purity levels less than the purity levels identified above. Indeed, with respect to use of the product as a reference standard, a purity level of about 93% or less is "substantially impure".

A substantially purified ivermectin product is also provided in accordance with the present invention. Such a product is contemplated to be useful as a reference standard for use in the regulatory approval process associated with therapeutic commercial use of ivermectin.

Ivermectin is a mixture of 5-O-demethyl-22,23-dihydroavermectin $A_{1a}$ (known as component $B_{1a}$) and 5-O-demethyl-25-de(1-methylpropyl)-22,23-dihydro-25-(1-methylethyl)avermectin $A_{1b}$ (known as component $B_{1b}$). Ivermectin contains not less than 95% component $B_{1a}$ plus component $B_{1b}$, calculated on the water-, alcohol-, and formamide-free basis. The empirical formula and molecular weight for ivermectin component $B_{1a}$ are $C_{48}H_{74}O_{14}$ and 875.10 grams/Mol, respectively. The empirical formula for ivermectin component $B_{1b}$ is $C_{47}H_{72}O_{14}$, and the molecular weight is 861.07 grams/Mol.

Substantially impure ivermectin is commercially available from a variety of sources. Additionally, microorganisms capable of producing ivermectin, e.g., *Streptomyces avermitilis*, can be cultured and substantially impure ivermectin isolated from such cultures according to standard techniques, such as those described in U.S. Pat. No. 4,429,042, the contents of which are herein incorporated by reference. A sample of *Streptomyces avermitilis* known as NRRL 8165 has also been deposited, without restriction as to availability, in the permanent culture collection of the American Type Culture Collection at 10801 University Blvd., Manassas, Va. 20110-2209, and has been assigned the accession number ATCC 31,267.

Structure of Ivermectin $B_{1a}$ ($C_{48}H_{74}O_{14}$, 875.10 g/Mol)

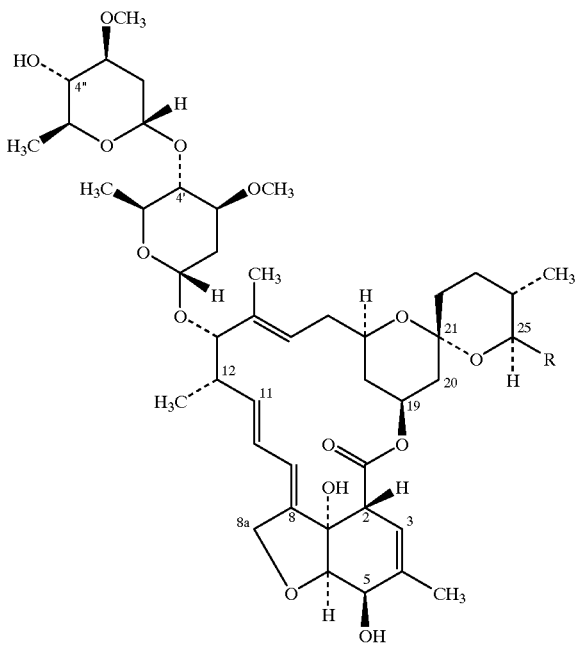

For Ivermectin $B_{1a}$ ($C_{48}H_{74}O_{14}$, 875.10 g/Mol)

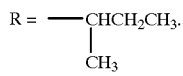

Structure of Ivermectin $B_{1b}$ ($C_{47}H_{72}O_{14}$, 861.07 g/Mol), is similar but the R Group at $C25=-CH(CH_3)_2$.

Another novel aspect of the invention is that the use of reversed-phase column chromatography substantially enriches an ivermectin component within the resulting purified ivermectin mixture. Particularly, the resulting purified mixture is enriched for the ivermectin $B_{1a}$ homolog. Enrichment for a single homolog facilitates use as a reference standard in that a single chemical entity provides for a better reference standard. As the number of correction factors decreases, the accuracy of analyses increases, and subsequent decisions made in the drug development process are likely to be better.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Example 1

Purification of Ivermectin

This Example describes the purification of ivermectin in order to produce reference standard quality material. In order to achieve this objective, three purification techniques were performed: (1) recrystallization (comparison), (2) normal-phase column flash chromatography (comparison), and (3) reversed-phase flash column chromatography (present invention).

(1) General procedure for recrystallization (comparison). Ivermectin was dissolved in a first solvent in which it was more soluble (e.g., methyl ethyl ketone, methylene dichloride, or ethanol) as compared to a second solvent. Then, the second solvent in which it was less soluble (e.g., straight-chain hexane, branched-chain hexane, cyclohexane, or water) was added until a slight turbidity persisted or crystallization began. This turbidity was cleared by adding several drops of the first solvent, and the solution was allowed to cool and to crystallize. The crystals were collected by filtration and washed free from mother liquor with the cold second solvent.

(2) General procedure for normal phase flash column chromatography (comparison). Ivermectin was dissolved in diethyl ether and applied to a silica gel flash chromatography column. Fractions were eluted with ethyl acetate:hexanes (0:1 to 2:1) and were monitored by thin layer chromatography (TLC). Fractions eluted with ethyl acetate:hexanes (2:1) were combined and concentrated on a rotary evaporator to afford a slightly yellow crystalline powder.

General procedure for reversed-phase flash column chromatography (present invention). $C_{18}$ silica gel was washed with methanol/water (100:0 to 0:100). Ivermectin was dissolved in methanol and applied to the column using a series of acetonitrile:methanol:water mixtures (0:5:5 to 5:4:1) as eluents. Four fractions of acetonitrile:methanol:water (5:2:3, 5:3:2, 5:3:1, and 5:4:1) were collected and concentrated on a rotary evaporator.

After the organic solvents were evaporated, the remaining mixture of water and white precipitate was extracted with diethyl ether. The ether extracts were combined and evaporated to give a white crystalline powder. Although this step was not a purification step, it facilitated the isolation of the product.

For the final product, 40–80 grams of ivermectin were separated at a time by reversed-phase flash column chromatography. One kilogram of $C_{18}$ silica gel was packed in a 4"×26" column. Four runs were performed on the column and a total of 222.5 grams ivermectin were chromatographed. The products from the four runs with purity greater than 98% were combined by dissolving in diethyl ether and concentrated in a rotary evaporator to afford a white crystalline powder. The final product was dried in vacuo at room temperature for 6 days. Final yield: 119.0 grams HPLC Analysis of Purified Product. The assay was carried out using the method described in Pharmacopeial Forum (PF), Vol. 23, No. 6, November-December 1997, p.5121–5124. HPLC Conditions:

| | |
|---|---|
| Instruments: | Hewlett Packard 1100 pump |
| Thermo Separation Products: | AS100 autosampler |
| Thermo Separation Products: | UV100 detector |
| Column: | Waters Symmetry $C_{18}$, 5 μm, 4.6 × 250 mm |
| Mobile Phase: | Acetonitrile:Methanol:Water (530:350:120) |
| Injection Volume: | 50 μL |
| Run Parameters: | Flow Rate: 1.0 mL/min Detection: UV 254 nm |

Approximate Retention Time(minutes):

| | |
|---|---|
| Ivermectin $B_{1b}$: | 19–20 |
| Ivermectin $B_{1a}$: | 24–25 |
| Standard: | Ivermectin |
| Samples: | Recrystallization samples, and samples isolated by column chromatography |
| Standard/Sample Preparation for HPLC Analysis: | Dissolve an accurately weighed quantity of ivermectin in methanol (1–2 mL to dissolve), and then dilute with mobile phase to obtain a standard solution having concentration of about 0.5 mg/mL and a sample solution having concentration of about 0.4 mg/mL |

Discussion of Example 1

Numerous attempts to improve the purity of ivermectin by re-crystallization involved many different recrystallization solvent systems (samples A-T, X-Y, Q-2 in Table 1). Although most of the recrystallizations produced crystalline materials, only a 3.0% improvement in purity was achieved at best (96.7% versus 93.7% for starting material). This suggested that some impurities might be buried in the crystalline structure and be difficult to remove by recrystallization.

Column chromatography was then used in an attempt to separate impurities from ivermectin. Two runs of normal phase silica gel flash column chromatography were tried (samples V and Nor-1 in Table 1). The HPLC assays of the resulting isolated products with the mobile phase ethyl acetate:hexanes (2:1) showed 96.1–96.9%. The results suggested that some polar impurities are likely not removed by the normal phase column chromatography.

Reversed-phase $C_{18}$ silica gel flash column chromatography was then used for the purification of ivermectin (sample Re-34 in Table 1), and the isolated samples from fractions of acetonitrile:methanol:water (5:3:2 and 5:3:1) consistently showed 98–99% purity by HPLC. This methodology was then scaled up to produce the final purified sample. HPLC analysis of the final substantially purified material showed 5% improvement as compared with substantially unpurified ivermectin (98% versus 93%).

Summarily, a 5% improvement in purity as determined by HPLC was achieved with reversed-phase flash column chromatography. Recrystallization and normal phase column chromatography methods, in contrast, produced only 0.2–3.2% improvement in purity.

TABLE 1

Summary of Experiments and Results

| Sample | Description (Purification Method) | Appearance of Sample | Weight (mg) Starting Material | Recovered | Recovery (%) | HPLC Results (%) |
|---|---|---|---|---|---|---|
| SM comparison | Staring Material, Ivermectin, substantially unpurified | Yellow-white powder | N/A[2] | N/A[2] | N/A[2] | 93.7 |
| A comparison | Recrystallized from methyl ethyl ketone and hexanes | Crystalline solid | 100 | 30 | 30 | 93.9 |
| B comparison | Recrystallized from acetone and $H_2O$ | Oil | 100.4 | N/A[2] | N/A[2] | NT[1] |
| C comparison | Recrystallized from methyl ethyl ketone and hexanes | White crystals | 101.7 | 67.3 | 66.2 | 96.7 |
| D comparison | Recrystallized from methyl ethyl ketone and hexanes | White crystals | 1000 | 789.4 | 78.9 | 95.4 |
| E comparison | Recrystallized from acetone and hexanes | Crystalline solid | 97.6 | 87.7 | 89.9 | NT[1] |
| F comparison | Recrystallized from $CH_2Cl_2$ and hexanes | Crystalline solid | 12 | 9.8 | 81.7 | NT[1] |
| G comparison | Recrystallized from $CH_2Cl_2$ and cyclohexane | Crystalline solid | 69.3 | 50.5 | 72.9 | NT[1] |
| H comparison | Recrystallized from diethyl ether | Oil | 43.6 | N/A[2] | N/A[2] | N/A[2] |
| I comparison | Recrystallized from ethanol and $H_2O$ | Crystalline solid | 100.1 | 92.3 | 92.2 | 94.0 |
| J comparison | Starting material dried in vacuo at room temperature overnight, then at 45° over $P_2O_5$ overnight | Crystalline solid | 58.3 | 58.2 | 99.8 | 94.4 |
| K comparison | Recrystallized from isopropanol and $H_2O$ | Oil | 105.8 | N/A[2] | N/A[2] | NT[1] |
| L | Recrystallized from | Crystalline | 105.8 | 93.5 | 88.4 | 94.2 |

TABLE 1-continued

Summary of Experiments and Results

| Sample | Description (Purification Method) | Appearance of Sample | Weight (mg) Starting Material | Recovered | Recovery (%) | HPLC Results (%) |
|---|---|---|---|---|---|---|
| M comparison | Recrystallized from ethanol and $H_2O$ | Crystalline solid | 89.8 | 79.6 | 88.6 | 94.8 |
| N comparison | Recrystallized from $CH_2Cl_2$ and cyclohexane | Oil | 103.4 | $N/A^2$ | $N/A^2$ | $NT^1$ |
| O comparison | Recrystallized from methanol and $H_2O$ | Crystalline solid | 96.3 | 84.8 | 88.1 | 95.2 |
| P comparison | Recrystallized from ethanol and $H_2O$ | Oil | 100.2 | $N/A^2$ | $N/A^2$ | $NT^1$ |
| Q comparison | Recrystallized from acetonitrile and $H_2O$ Recrystallized from cyclohexane and acetone, refrigerated for 10 days | Crystalline solid | 74.7 | 59.3 | 79.4 | 92.4 |
| R comparison | Recrystallized from isopropanol | Oil | 82.5 | $N/A^2$ | $N/A^2$ | $NT^1$ |
| S comparison | Recrystallized from acetone, refrigerated for 10 days | Oil | 43.6 | $N/A^2$ | $N/A^2$ | $NT^1$ |
| T comparison | Recrystallized from acetonitrile | Oil | 103.4 | $N/A^2$ | $N/A^2$ | $NT^1$ |
| U comparison | Dried in vacuo at room temperature overnight | Crystalline solid | 151.8 | $N/A^{2,3}$ | $N/A^2$ | 94.5 |
| V comparison | Normal phase chromatography | Slight yellow solid | 1030 | 958.8 | 93.1 | 96.1 |
| X comparison | Recrystallized from methyl ethyl ketone and hexanes, refrigerated for 1 day | Crystalline solid | 79.8 | 43.2 | 54.1 | $NT^1$ |
| Q-2 comparison | Recrystallized from cyclohexane and acetone, refrigerated | No crystals observed | 51.4 | $N/A^2$ | $N/A^2$ | $NT^1$ |
| Y comparison | Recrystallized from hexanes and acetone, refrigerated | Crystalline solid | 65.3 | 46.6 | 71.4 | $NT^1$ |
| Nor-1 comparison | Normal phase column chromatography | Slight yellow solid | 401.5 | 364.6 | 91.0 | 96.9 |
| Re-34 present invention | Reversed phase column chromatography on 1000 g $C_{18}$ | White crystalline powder | 50.06g | 34.9g | 69.7 | 99.0 |

$NT^1$: Not Tested.
$N/A^2$: Not Applicable.
[3] Analyst inadvertently forgot to weigh product.

Example 2

Characterization of Ivermectin

This Example characterizes a purified ivermectin reference standard material produced in accordance with the process of the present invention. The structure and identification of the reference standard ivermectin was determined by a combination of nuclear magnetic resonance (NMR), mass spectrometry (MS), infrared (IR) and ultraviolet (UV) spectroscopy, elemental analysis, x-ray powder diffraction (XRPD), and Identification B: UV. Purity data was determined by differential scanning calorimetry (DSC), thermal gravimetric analysis (TGA), color and clarity of solution, heavy metals determination, Karl Fischer water titration, specific rotation, residue on ignition, residual volatiles (limit of alcohol and formamide) and HPLC.

The experimental methods described in this Example are recognized in the art. Detailed methods for these experiments can be found in Pharmacopeial Forum (PF), Vol. 23, No. 6 (November-December 1997) 5121–5124. Additionally, the techniques are described in the U.S. Pharmacopeia (USP) at the following volume and page numbers: 23:851, 23:891, 23:231, 23:921, 23:781, 23:281 and 23:281. The disclosure of each of these references is incorporated herein by reference as if fully set forth herein.

Experiments

Appearance. A small amount of ivermectin reference standard was placed on a sheet of clean white paper for examination. The structure of ivermectin $B_{1a}$ is shown above.

| | |
|---|---|
| Mass Spectrometer: | Micromass Platform II |
| Ionization Mode: | Positive and Negative Ion Fast Atom Bombardment (FAB) |
| Data System: | Digital Celebris XL 590 |
| Software: | Micromass Mass Lynx NT version 2.22 |
| Data Type: | Compressed Centroid |
| Scan Range: | m/z 100–2000 |
| Cycle Time: | 19 seconds |

Mass Scale Calibration: The Micromass Platform II mass spectrometer mass scale was calibrated prior to data collection. The calibration procedure was performed in positive ion Fast Atom Bombardment (FAB) using a saturated cesium iodide solution.

Sample Analysis: While in positive ion FAB mode, a drop of 3-nitrobenzyl alcohol (Aldrich, 98%) was applied to a cleaned probe tip, the acquisition was initiated and the probe inserted into the ion source to provide a background spectrum. After approximately one (1) minute, the probe was removed. Another drop of 3-nitrobenzyl alcohol was applied and a small amount of sample was dissolved on the probe. The probe was reinserted into the ion source to provide a sample spectrum.

The ion source mode was switched to negative ion FAB and a new acquisition initiated with the remaining sample left from the positive ion FAB analysis. After a few acquisitions, the probe was removed and another drop of 3-nitrobenzyl alcohol was applied and the probe reinserted to provide a background spectrum for comparison.

Nuclear Magnetic Resonance (NMR). The sample for $^1$H and $^{13}$C NMR was prepared by placing a spatula tip of material in a 5 mm NMR tube and adding the contents of a 1 g ampoule of $CDCl_3$. The spectra were obtained on a Bruker Advance DRX 400 spectrometer operating in Fourier Transform (FT) mode. The data were processed on the spectrometer using Bruker's XWINNMR™ software. The $^1$H NMR data were Fourier transformed and baseline corrected. Prior to transformation of the $^{13}$C NMR data a line broadening of 2 Hz was applied. The $^1$H NMR spectrum is referenced relative to residual $CHCl_3$ ($\delta$=7.24 ppm) and the $^{13}$C NMR spectrum is referenced relative to the $CDCl_3$ solvent ($\delta 32$ 77.0 ppm).

Infrared (IR) Spectroscopy. Ivermectin (5 mg) was mixed with potassium bromide (500 mg) and ground to a fine powder to give a 1% dispersion of the sample. An aliquot of this mixture was then pressed into a KBr pellet and scanned using a Nicolet Impact 400 IR spectrophotometer. Air was used to collect the blank scan on the IR spectrophotometer.

Ultraviolet (UV)-Visible Spectroscopy. A solution of ivermectin was prepared at a concentration of $2.29 \times 10^{-5}$ Moles/L in methanol and scanned using a Hewlett Packard 8452A Diode Array Spectrophotometer. Methanol was used as an instrument blank for this study.

Elemental Analysis. Ivermectin was evaluated for carbon, nitrogen, hydrogen, and oxygen content.

X-Ray Powder Diffraction (XRPD). XRPD analyses were carried out on a Shimadzu XRD-6000 X-ray powder diffractometer equipped with a fine-focus X-ray tube using Cu Kα radiation (1.5406 Å). The tube power was set at 40 kV and 40 mA. The divergence and scattering slits were set at 1° and the receiving slit was set at 0.15 mm. Diffracted radiation was detected by an NaI scintillation detector. A θ/2θ continuous scan at 3°/minute (0.4 second/0.02° step) from 4 to 40° 2θ was used. A silicon standard was run each day to check the x-ray tube alignment. The sample was prepared for analysis by pressing it with a spatula onto a quartz sample holder.

Differential Scanning Calorimetry (DSC). The DSC analysis was performed using a Seiko DSC220C with the nitrogen flow rate set at 100 mL/minute. A DSC pan was filled with 10 mg of sample and subjected to the following temperature program. The pan was heated from 25° C. to 150° C. at 10° C./minute, cooled to 25° C. at 10° C./minute, and heated to 300° C. at 10° C./minute. Following this cycle the sample pan was reheated from 25° C. to 350° C. at 10° C./minute. To document all the thermal events from this series of experiments on a single thermogram a new 10 mg sample was prepared and subjected to DSC analysis from 25° C. to 350° C. at 10° C./minute. An empty aluminum pan was used as the reference.

Thermal Gravimetric Analysis (TGA). The TGA study was performed using a Seiko TG/DTA220 with the nitrogen flow rate set to 100 mL/minute. An open aluminum pan filled with 10 mg of sample was subjected to analysis from 30° C. to 350° C. at 10° C./minute. An empty aluminum pan was used as the reference.

Identification B: Ultraviolet (UV) Absorption. The Identification B: UV absorption was performed on a 19.8 µg/mL solution of ivermectin in methanol. The absorptivity (absorbance/concentration) at the wavelength of maximum absorbance at about 245 nm was determined and should be between 37.2 and 39.2, calculated on the water, alcohol, and diethyl ether-free basis.

Color and Clarity of Solution. Color and clarity of solution was performed according to PF volume 23, number 6, November-December 1997, pages 5121–5124, using 1 gram of ivermectin dissolved in 50 mL of toluene.

Heavy Metals. Heavy metals analysis was performed according to USP 23:231 using 1 gram of sample.

Karl Fischer Water. Water content was evaluated using volumetric Karl Fischer titration. The sample was injected directly into the titration vessel and the water content determined. The sample was injected in duplicate and 200 mg of ivermectin, accurately weighed, was used for each injection. Water values were determined using a Mitsubishi CA-06 Moisturemeter.

Specific Rotation. Specific rotation was performed using a photoelectric polarimeter with a temperature-controlled 1 dm sample cell. A 25 mg/mL solution of ivermectin was prepared in methanol. A single determination of the sample solution, corrected for the solvent blank, was performed. Specific rotation is calculated as follows:

$$[\alpha]_\lambda^t = \frac{100a}{Ic}$$

where [α] is the specific rotation at temperature, t, and wavelength, λ. The concentration of the analyte, c, on the volatiles free basis is given in grams per 100 mL, while the pathlength, I, is given in decimeters. The observed rotation is represented by the letter "a".

Residue on Ignition. Residue on ignition was performed according to USP 23:281 using 1 gram of sample in a platinum crucible.

Limit of Alcohol and Formamide. The gas chromatography (GC) volatiles test was performed using a modified procedure from PF, volume 23, number 6, November-December 1997, pages 5121–5124. The ivermectin sample was tested for ethanol and diethyl ether using this modified procedure. The test for formamide was not conducted since any of this solvent present in the sample would have been removed during the reversed-phase column chromatography purification of ivermectin. The sample was tested for diethyl ether since this solvent was used in the final step of the ivermectin purification and was likely to be present in the sample.

Standard Preparation. Two standard solutions were prepared for the GC analysis at appropriate concentrations to bracket the amount of ethanol and diethyl ether in the ivermectin sample solutions. One standard solution of ethanol at 0.00015 mL/mL and diethyl ether at 0.0004 mL/mL was prepared in deionized water. The second standard solution of ethanol at 0.000015 mL/mL and diethyl ether at 0.00004 mL/mL was also prepared in deionized water. Both solutions were extracted using 2.0 mL of m-xylene. The phases of each standard solution were separated by centrifugation. The extracted aqueous phase from this procedure was used as the standard solution.

Sample Preparation. Samples were prepared by dissolving 120 mg of ivermectin, accurately weighed, into a 15 mL centrifuge tube. A 2.0 mL aliquot of m-xylene was added to the centrifuge tube containing the ivermectin. The m-xylene solution was extracted in duplicate using 2.0 mL of deionized water. The two phases were separated by centrifugation. After the second extraction the two aqueous portions were combined to give the sample solution.

GC System Components and Conditions.

| Instrument: | Hewlett Packard Gas Chromatograph |
|---|---|
| Flame Ionization Detector: | Hewlett Packard Chemstation ™ Control Software |
| Column: | Supelco Chromosorb ™ 101, Mesh 80/100, 1.8 m, 2 mm i.d. |
| GC Oven: | |
| Injector Temperature: | 190° C. |
| Oven Temperature: | 130° C. hold for 4 minutes |
| | Ramp at 40° C./minute to 180° C. |
| | 180° C. hold for 20 minutes |
| | Post run: 130° C. hold for 3 minutes |
| Detector: | FID (Flame Ionization Detector) |
| Temperature: | 250° C. |
| Hydrogen Flow Rate: | 40 mL/minute |
| Air Flow Rate: | 450 mL/minute |
| Nitrogen Flow Rate: | 20 mL/minute |
| Carrier Gas Flow (Helium): | 34 mL/min |
| Injection volume: | 2 μL |
| Data System: | PE Nelson Turbochrom 4.1 |

HPLC Purity. The chromatographic purity was performed using the chromatographic system described in PF, volume 23, number 6, November-December 1997, pages 5121–5124.

HPLC Sample Preparation. Samples were prepared by accurately weighing 50 mg of ivermectin drug substance into a 100 mL volumetric flask dissolving in and diluting to volume with mobile phase.

HPLC System Components:

| Instrument: | Thermo Separations P 100 isocratic pump |
|---|---|
| | Thermo Separations AS 100 autosampler |
| | Thermo Separations UV 100 detector |
| Column: | Waters Symmetry $C_{18}$, 4.6 × 250 mm, 5 μm particle size |
| Mobile Phase: | Acetonitrile:Methanol:Water (53:35:12) |
| Flow Rate: | 1.0 mL/min |
| Temperature: | Ambient |
| Detection: | 254 nm |
| Injection: | 50 μL |
| Data System: | PE Nelson Turbochrom 4.1 |
| Sample Diluent: | Mobile Phase |

Calculation of Standard Purity. The standard purity was calculated by adding the percent area under the curve for Ivermectin $B_{1a}$ and $B_{1b}$ to give an uncorrected purity value. This value was then corrected for volatiles by subtracting the percent water, ethanol and diethyl ether found to be present in the ivermectin sample.

Results

Electrospray Mass Spectrometry. Because of the low expected proton affinity of ivermectin (due to the absence of heteroatoms such as nitrogen), no protonated molecular ion was observed in a positive ion FAB mass spectrum. Instead a sodiated species was observed at m/z 897, which is consistent with a monoisotopic molecular weight of 874 Da. No evidence for chlorine, bromine, sulfur or other heteroatoms was observed in the molecular-ion region to suggest the presence of any elements other than carbon, hydrogen, oxygen or nitrogen. The largest peaks observed in the mass spectrum likely arise from the fragmentation of the two exocyclic pyranose rings (m/z 569) and subsequent dehydration (m/z 551). A small peak was seen at m/z 713, and thus, the loss of one pyranose is also possible and is consistent with the structure of ivermectin. Negative ion FAB mass spectrum for ivermectin confirmed the monoisotopic weight because of the observation of a prominent deprotonated molecular ion at m/z 873 and the probable 3-nitrobenzyl alcohol adduct at m/z 1027.

The FAB mass spectrum obtained from ivermectin isolated in Example 1 was clearly consistent with the molecular structure of this chemical entity. The monoisotopic molecular weight was confirmed to be 874 Da. The mass spectral behavior was consistent with a molecule containing only carbon, hydrogen and oxygen.

Nuclear Magnetic Resonance (NMR). Because of the chemical structure of the investigated molecule, the obtained NMR data were complex. Since no reference material was available for direct comparison, the data obtained herein was compared to available literature data. While literature references give only an incomplete listing of the $^1$H NMR signals of ivermectin $B_{1a}$, a complete listing of the carbon chemical shifts, including their assignments, was available.

$^{13}$C NMR spectrum of ivermectin produced in accordance with the process of the present invention is summarized in Table 2. Table 2 lists the observed chemical shifts and compares them to the reported chemical shifts and their literature assignments. The chemical structure of ivermectin B1a, including numbering, is presented above. Overall, the correlation is good for $^{13}$C NMR chemical shift data. The deviations likely are due to matrix effects, since the sample reported in the literature contained a significant amount of formamide.

$^1$H NMR spectrum of ivermectin produced in accordance with the process of the present invention is summarized in Table 3. Unfortunately, the literature reference does not give a complete listing of the determined $^1$H NMR parameters. Table 3 compares the observed data to the literature values and assignments. The data correlates well and the observed chemical shifts are consistently $\Delta\delta(^1H)$ 0.04 to 0.05 ppm lower than those reported.

The NMR data obtained on ivermectin produced in accordance with the process of the present invention are consistent with that of a single homolog of ivermectin. While the baseline in the region from $\delta(^1H)$ 1.1–0.9 ppm demonstrates that the material is not homogeneous by $^1$H NMR, the presence of a second ivermectin species is not conclusively indicated.

Infrared (IR) Spectroscopy. The IR spectrum of ivermectin and Spectral Band assignments are summarized in Table 4. The observed bands are consistent with the structure of ivermectin.

Ultraviolet(UV)-Visible Spectroscopy. The UV spectrum analysis of ivermectin in methanol showed two absorption maxima; at 204 nm ($\epsilon_{204}$=11,053 AU·cm$^{-1}$·M$^{-1}$) and 246 nm($\epsilon_{246}$=32,618 AU·cm$^{-1}$·M$^{-1}$). The absorption maximum at 246 nm exhibits two shoulders; at 240 nm ($\epsilon_{240}$=29,958 AU·cm$^{-1}$·M$^{-1}$) and 254 nm($\epsilon_{254}$=21,270 AU·cm$^{-1}$·M$^{-1}$). These absorption bands are characteristic of a conjugated structure.

Elemental Analysis. The results of the elemental analysis can be seen in Table 5. The results are consistent with the theoretical results.

X-Ray Powder Diffraction (XRPD). The sample was found to be amorphous, as evidenced by the broad amorphous halo in the region 7–30 ° 2θ of the XRPD pattern.

Differential Scanning Calorimetry (DSC). DSC analysis of ivermectin showed one major thermal event at approximately 309° C., which represents a solid-liquid transition. The thermal event above approximately 325° C. represents thermal degradation of the sample.

Thermal Gravimetric Analysis (TGA). TGA analysis of ivermectin indicated that the weight of the sample remains essentially constant until approximately 294° C. Above this temperature there is a rapid loss of sample weight which corresponds to the thermal degradation seen in the DSC analysis.

Identification B: Ultraviolet (UV) absorption. The absorptivity in methanol at 246 nm for the ivermectin sample was 37.7 AU/(mg/mL).

Color and Clarity of Solution. The test solution was colorless and exhibited an absorbance less than 0.024 AU at 440 nm (Actual absorbance at 440 nm was 0.0027 AU, approximate solution concentration was 20 mg/mL).

Heavy Metals. The test solution does not exceed the heavy metals limit of 0.002% (w/w).

Karl Fischer Water. The ivermectin sample was determined to contain 0.62% (w/w) water.

Specific Rotation. Specific rotation calculated on the volatiles free basis was determined as −19.3° at 20° C., 589 nm.

Residue on Ignition. The residue on ignition was less than 0.01% (w/w).

Limit of Alcohol and Formamide. The volatiles were assessed by gas chromatography (GC) and the ivermectin sample was found to contain 0.06% alcohol and 0.55% diethyl ether. No formamide was detected in the sample.

HPLC Purity. Chromatographic purity was assessed by calculating the percent area under the curve (% AUC) for all impurities and actives present in the chromatographic runs. Table 6 lists the % AUC values for the active drug substances and the impurities with values greater than 0.05% AUC.

Calculation of Standard Purity. The standard purity is the % AUC of avermectin $B_{1a}$ and Ivermectin $B_{1b}$ minus the water and volatiles content. An example calculation is shown below.

| | |
|---|---|
| 95.15% | Ivermectin $B_{1a}$ |
| +2.22% | Ivermectin $B_{1b}$ |
| 97.37% | Ivermectin $B_{1a}$ + $B_{1b}$ |
| −0.62% | water |
| −0.06% | ethanol |
| −0.55% | diethyl ether |
| 96.14% | standard purity (w/w) |

Appearance. The ivermectin reference standard is a white crystalline powder free from visible contamination.

The NMR, MS, IR, and UV spectral data as well as the XRPD data support the structure of ivermectin shown hereinabove. The molecular formula of ivermectin is supported by the elemental analysis data. In addition, the identity of ivermectin is confirmed by the Identification B: UV test. The HPLC data indicates that the reference standard has a chromatographic purity of 97.37% AUC. The additional purity assessment data (DSC, TGA, color and clarity of solution, heavy metals determination, Karl Fischer water titration, specific rotation, residue on ignition, and residual volatiles) presented above are consistent with the HPLC results. For quantitative analysis of other samples the purity of ivermectin reference standard produced in accordance with the process of the present invention is 96.14%. This standard purity accounts for water and volatiles in the reference standard.

TABLE 2

Literature $^{13}$C NMR Data for Ivermectin $B_{1a}$ and Experimental $^{13}$C NMR Data for Ivermectin (Chemical Shifts in ppm).

| Carbon Assignment | Literature Value | Experimental Value |
|---|---|---|
| C(1) | 173.7 | 173.8 |
| C(8) | 139.6 | 139.6 |
| C(11) | 138.0 | 138.0 |
| C(4) | 137.8 | 138.0 |
| C(14) | 135.0 | 135.0 |
| C(10) | 124.7 | 124.7 |
| C(9) | 120.4 | 120.4 |
| C(3) | 118.4 | 118.3 |
| C(15) | 118.1 | 118.0 |
| C(1") | 98.5 | 98.5 |
| C(21) | 97.5 | 97.5 |
| C(1') | 94.8 | 94.7 |
| C(13) | 81.8 | 81.7 |
| C(4) | 80.5 | 80.3 |
| C(7) | 80.4 | 79.3 |
| C(6) or C(3') | 79.4 | 79.0 |
| C(6) or C(3') | 79.3 | ND |
| C(3") | 78.2 | 78.1 |
| C(25) | 76.5 | ND |
| C(4") | 76.1 | 76.0 |
| C(5") | 68.7 | 68.6 |
| C(17) or C(19) | 68.4 | 68.4 |
| C(8a) | 68.2 | 68.1 |
| C(5) | 67.7 | 67.7 |
| C(5"), C(17) or C(19) | 67.2 | 67.2 |
| $OCH_3$ | 56.5 | 56.5 |
| $OCH_3$ | 56.4 | 56.4 |
| C(2) | 45.8 | 45.7 |
| C(20) | 41.2 | 41.1 |
| C(12) | 39.8 | 39.7 |
| C(16) | 36.9 | 36.9 |
| C(22) | 35.8 | 35.7 |
| C(26) | 35.5 | 35.4 |
| C(2') or C(18) or C(2") | 34.5 | 34.5 |
| C(2') or C(18) or C(2") | 34.3 | 34.1 |
| C(2') or C(18) or C(2") | 34.1 | 34.1 |
| C(24) | 31.2 | 31.2 |
| C(23) | 28.1 | 28.0 |
| C(27) | 27.3 | 27.3 |
| NA | NR | 20.2 |
| C(4a) | 19.9 | 19.9 |
| C(6") | 18.4 | 18.4 |
| C(6') | 17.7 | 17.7 |
| C(24a) | 17.4 | 17.4 |
| C(14a) | 15.1 | 15.1 |
| C(26a) | 12.4 | 12.4 |
| C(28) | 12.1 | 12.1 |

TABLE 3

Literature $^1$H NMR Data for Ivermectin $B_{1a}$ and Experimental $^1$H NMR Data for Ivermectin

| Proton Assignment | Literature Value | Experiment Value | Observed Parameters |
|---|---|---|---|
| C(9)—H | 5.87 | 5.83 | 1H, dm, J = 8.08 Hz |
| C(10)—H, C(11)—H | 5.74 | 5.70 | 2H, m |
| C(3)—H | 5.43 | 5.36 | 1H, s |
| C(1")—H | 5.40 | 5.33 | 1H, d, J = 5.01 Hz |
| C(19)—H | 5.34 | 5.32 | 1H, m |
| C(15)—H | 4.98 | 4.95 | 1H, dm, J = 9.50 Hz |
| C(1')—H | 4.78 | 4.75 | 1H, d, J = 3.27 Hz |
| C(8a)—H$_2$ | 4.69 | 4.65 | 2H, m |
| C(5)—H | 4.30 | 4.27 | 1H, br. d, J = 5.33 Hz |
| O—H | 4.17 | ~4.10 | 1H, br. s |
| C(6)—H | 3.98 | 3.94 | 1H, d, J = 6.22 Hz |
| C(13)—H | 3.95 | 3.91 | 1H, br. s |
|  | NR | 3.80 | 1H, m |
|  | NR | 3.74 | 1H, m |
|  | NR | 3.60 | 1H, m |
|  | NR | 3.59 | 1H, m |
|  | NR | 3.44 | 2H, m |
| O—CH3 | 3.44 | 3.40 | 3H, s |
| O—CH3 | 3.42 | 3.39 | 3H, s |
|  | NR | 3.26 | 1H, app. q, J= 2.23 Hz |
|  | NR | 3.21 | 1H, t, J = 9.01 Hz |
|  | NR | 3.19 | 1H, dm, J = 7.75 Hz |
| C(4")—H | 3.17 | 3.13 | 1H, t, J = 9.11 Hz |
| C(12)—H | 2.52 | 2.49 | 1H, m |
|  | NR | 2.22 | 5H, m |
| C(20)—Heq | 1.99 | 1.95 | 1H, dd, J = 12.16, 3.89 Hz |
| C(4)—CH3 | 1.88 | 1.84 | 3H, s |
| C(18)—Heq | 1.78 | 1.73 | 1H, m |
|  | NR | 1.63 | 1H, dm, J = 12.16 Hz |
| C(14)—CH3 | 1.51 | NA |  |
|  | NR | 1.47 | 14H, m |
| C(5')—CH3 or C(5")—CH3 | 1.30 | 1.25 | 3H, d, J = 6.29 Hz |
| C(5')—CH3 or C(5")—CH3 | 1.27 | 1.22 | 3H, d, J = 6.30 Hz |
|  | NR | 1.18 | 1H, t, J = 7.03 Hz |
| C(12)—CH3 | 1.18 | 1.13 | 2H, d, J = 6.93 Hz |
| C(28)—CH3 | 0.93 | 0.90 | 3H, t, J = 7.37 Hz |
| C(26)—CH3 | 0.87 | 0.82 | 3H, d, J = 6.71 Hz |
| C(24)—CH3 | 0.80 | 0.76 | 3H, d, J = 5.57 Hz |

TABLE 4

Infrared Band Assignments for Ivermectin

| Band (cm$^{-1}$) | Assignment |
|---|---|
| 3468 | O—H stretch |
| 2967 | Symmetric Aliphatic C—H Stretch |
| 2932 | Asymmetric Aliphatic C—H Stretch |
| 1719 | C=O stretch |
| 1197, 1120, 1045, 986 | C—O stretch (4 bands between approximately 1000 and 1200 cm$^{-1}$) |

TABLE 5

Elemental Analysis Results for Ivermectin (uncorrected for volatiles)

| Element | $B_{1a}$ | $B_{1b}$ | Found |
|---|---|---|---|
| % Carbon | 65.9 | 65.6 | 65.22 |
| % Hydrogen | 8.5 | 8.4 | 8.70 |
| % Oxygen | 25.6 | 26.0 | 25.48 |

TABLE 6

HPLC Purity of Actives and Impurities for Ivermectin

| Relative Retention Time | Retention Time (min) | Percent Area under Curve[1] (% AUC) |
|---|---|---|
| 0.47 | 12.28 | 0.16 |
| 0.61 | 15.88 | 0.13 |
| 0.74 | 19.36 | 0.19 |
| 0.78($B_{1b}$) | 20.30 | 2.22 |
| 0.84 | 21.98 | 0.15 |
| 1.00($B_{1a}$) | 26.07 | 95.15 |
| 0.87 | 22.64 | 0.05 |
| 1.24 | 32.40 | 0.70 |
| 1.37 | 35.66 | 1.15 |

[1]Impurities with % AUC values less than 0.05% are not listed in this table.

Example 3

Large Scale Purification of Ivermectin using Reversed-Phase Flash Column Chromatography Column Preparation. One kilogram of $C_{18}$ silica gel (40 micron ($\mu$), purchased from J.T.Baker) is packed in a 4"×24" column, and washed with methanol (8000 mL), then with methanol/water (5:1, 5:2, 5:3, and 5:4; each 6000 mL), and then with water (6000 mL), and then backwashed with methanol/water (1:5, 2:5, and 5:5; each 6000 mL).

Chromatographic Purification. 40 grams of ivermectin is dissolved in methanol (200 mL) in a 400 mL beaker and is applied to the column carefully. The beaker is then rinsed with methanol (20 mL) and added to the column. The column is then eluted with a series of mobile phases in accordance with the following predetermined profile.

1). MeOH/H$_2$O (1:1): 4000 mL.

2). Acetonitrile/methanol/H$_2$O (5:2:3): 4000 mL.

3). Acetonitrile/methanol/H$_2$O (5:2.5:2.5): 4000 mL.

4). Acetonitrile/methanol/H$_2$O (5:3:2): 8000 mL.

5). Acetonitrile/methanol/H$_2$O (5:3:1): 8000 mL.

TLC shows spots of desired product in mobile phases 3) through 5). However, all of 1), 2), and 3), the first 2–2.5 L of 4), and the last 1–1.5 L of 5) are discarded in order to maximize the purity of eventually isolated product.

The desired collected fractions are combined and concentrated under reduced pressure on a rotary evaporator. After the organic solvents are evaporated, the remaining mixture of water and white precipitate are extracted with ether (HPLC grade, 3×150 mL). The ether extracts are combined and evaporated to give a white crystalline powder and dried in vacuo over P$_2$O$_5$ for 5–7 days.

Column backwash. After elution, the column is washed with methanol (8000 mL) and methanol/H$_2$O (1:1, 8000 mL) in preparation for the next chromatography. All solvents used should be HPLC grade, and water should be deionized (DI) water.

It will be understood that various details of the invention may be changed without departing from the scope of the invention. Furthermore, the foregoing description is for the purpose of illustration only, and not for the purpose of limitation--the invention being defined by the claims.

What is claimed is:

1. A process for purifying ivermectin, comprising:
   (a) obtaining substantially impure ivermectin;
   (b) loading the substantially impure ivermectin on a chromatographic column suitable for reversed-phase flash column chromatography;
   (c) initiating reversed-phase flash chromatography by applying a first volume of an eluent mixture to the column, the eluent mixture comprising acetonitrile, lower alkyl alcohol and water;
   (d) establishing an eluent gradient in the column by adding a series of subsequent volumes of the acetonitrile/lower alkyl alcohol/water eluent mixture to the column, wherein each of the first and the subsequent volumes of the eluent mixture has a ratio of acetonitrile to lower alkyl alcohol to water that varies according to a predetermined profile; and
   (e) collecting predetermined fractions eluted from the column, the predetermined fractions comprising substantially purified ivermectin.

2. The process of claim 1, wherein the chromatographic column comprises a $C_{18}$ silica gel column.

3. The process of claim 1, wherein the predetermined profile of ratios of acetonitrile to lower alkyl alcohol to water in the first and the subsequent volumes of eluent mixture comprises a range from 0:5:5 to 5:4:1.

4. The process of claim 3, wherein the predetermined fractions collected in step (d) correspond to four respective volumes of eluent mixture wherein the acetonitrile, lower alkyl alcohol and water are present in the eluent mixture in the following four respective ratios 5:2:3, 5:3:2, 5:3:1 and 5:4:1.

5. The process of claim 3, wherein the predetermined fractions collected in step (d) correspond to two respective volumes of eluent mixture wherein the acetonitrile, lower alkyl alcohol and water are present in the eluent mixture in the following two respective ratios 5:3:2 and 5:3:1.

6. A process for purifying ivermectin, comprising:
   (a) obtaining substantially impure ivermectin;
   (b) loading the substantially impure ivermectin on a chromatographic column suitable for reversed-phase flash column chromatography;
   (c) initiating reversed-phase flash chromatography by applying a first volume of an eluent mixture to the column, the eluent mixture comprising acetonitrile, methanol and water;
   (d) establishing an eluent gradient in the column by adding a series of subsequent volumes of the acetonitrile/methanol/water eluent mixture to the column, wherein each of the first and the subsequent volumes of the eluent mixture has a ratio of acetonitrile to methanol to water that varies according to a predetermined profile; and
   (e) collecting predetermined fractions eluted from the column, the predetermined fractions comprising substantially purified ivermectin.

7. The process of claim 6, wherein the chromatographic column comprise a $C_{18}$ silica gel column.

8. The process of claim 6, wherein the predetermined profile of ratios of acetonitrile to methanol to water in the first and the subsequent volumes of eluent mixture comprises arrange from 0:5:5 to 5:4:1.

9. The process of claim 8, wherein the predetermined fractions collected in step (d) correspond to four respective volumes of eluent mixture wherein the acetonitrile, methanol and water are present in the eluent mixture in the following four respective ratios 5:2:3, 5:3:2, 5:3:1 and 5:4:1.

10. The process of claim 8, wherein the predetermined fractions collected in step (d) correspond to two respective volumes of eluent mixture wherein the acetonitrile, methanol and water are present in the eluent mixture in the following two respective ratios 5:3:2 and 5:3:1.

11. A process for purifying ivermectin, comprising:
    (a) obtaining substantially impure ivermectin;
    (b) loading the substantially impure ivermectin on a chromatographic column suitable for reversed-phase flash column chromatography;
    (c) initiating reversed-phase flash chromatography by applying a first volume of an eluent mixture to the column, the eluent mixture comprising acetonitrile, methanol and water;
    (d) establishing an eluent gradient in the column by adding a series of subsequent volumes of the acetonitrile/methanol/water eluent mixture to the column, wherein each of the first and in the subsequent volumes of the eluent mixture has a ratio of acetonitrile to methanol to water that varies according to a profile comprising a range from about 0:5:5 to about 5:4:1; and
    (e) collecting predetermined fractions eluted from the column, the predetermined fractions comprising substantially purified ivermectin.

12. The process of claim 11, wherein the chromatographic column comprises a $C_{18}$ silica gel column.

13. A The process of claim 11, wherein the predetermined fractions collected in step (d) correspond to four respective volumes of eluent mixture wherein the acetonitrile, methanol and water are present in the eluent mixture in the following four respective ratios 5:2:3, 5:3:2, 5:3:1 and 5:4:1.

14. The process of claim 11, wherein the predetermined fractions collected in step (d) correspond to two respective volumes of eluent mixture wherein the acetonitrile, methanol and water are present in the eluent mixture in the following two respective ratios 5:3:2 and 5:3:1.

15. The process of any of claims 1, 6 or 11, wherein a purity level of the substantially purified ivermectin comprises at least about 98%.

* * * * *